United States Patent [19]

Jayne

[11] Patent Number: 5,542,428
[45] Date of Patent: Aug. 6, 1996

[54] METHOD AND APPARATUS FOR REMOVING ARTIFACT ENCOUNTERED DURING AUTOMATIC BLOOD PRESSURE MEASUREMENTS

[75] Inventor: Cynthia P. Jayne, Redmond, Wash.

[73] Assignee: SpaceLabs Medical, Inc., Redmond, Wash.

[21] Appl. No.: 409,512

[22] Filed: Mar. 23, 1995

[51] Int. Cl.⁶ .................................................. A61B 5/00
[52] U.S. Cl. ........................................... 128/681; 128/682
[58] Field of Search ............................ 128/672, 677–683, 128/687

[56] References Cited

U.S. PATENT DOCUMENTS

| | | | |
|---|---|---|---|
| 4,706,684 | 11/1987 | Sorensen et al. | 128/677 |
| 4,777,959 | 10/1988 | Wallach et al. | 128/677 |
| 4,785,820 | 11/1988 | Brooks | 128/681 |
| 4,799,492 | 1/1989 | Nelson | 128/672 |
| 4,905,704 | 3/1990 | Walloch | 128/682 |
| 4,924,873 | 5/1990 | Sorensen | 128/677 |
| 5,014,714 | 5/1991 | Millay et al. | 128/672 |
| 5,280,790 | 1/1994 | Brooks | 128/681 |
| 5,337,750 | 8/1994 | Walloch | 128/680 |

*Primary Examiner*—Angela D. Sykes
*Assistant Examiner*—Robert L. Nasser, Jr.
*Attorney, Agent, or Firm*—Seed and Berry LLP

[57] ABSTRACT

A blood pressure monitoring system having a blood pressure cuff, an air pump applying pressurized air to the cuff; a valve to selectively vent the cuff, and a pressure transducer generating a signal indicative of the pressure in the cuff corresponding to an occlusive pressure exerted by the cuff on an artery and a transient fluid pressure in the cuff indicative of the amplitude of an oscillometric pulse. An analog-to-digital converter connected to the transducer samples the output of the transducer and generates respective digital samples corresponding to the output of the transducer. A processor receives the respective digital samples corresponding to the signal indicative of the steady state fluid pressure in the cuff and the signal corresponding to the amplitude of the oscillometric pulses. The processor also records in a table the steady state fluid pressure at which each measurement is made and the amplitude of the peak oscillometric pulses at such pressure. The processor also determines all local maxima of the amplitude of the oscillometric peaks in the table, and examines the longest sequences of the amplitudes of the oscillometric peaks at cuff pressures adjacent to the cuff pressure at which each of the local maxima was obtained. Then, the processor chooses one of the local maxima as a true maximum value based on a comparison of the longest sequences adjacent to each of the local maxima and computes blood pressure using this value.

11 Claims, 6 Drawing Sheets

METHOD AND APPARATUS FOR REMOVING ARTIFACT ENCOUNTERED DURING AUTOMATIC BLOOD PRESSURE MEASUREMENTS

DESCRIPTION

1. Technical Field

This invention relates to the automatic measurement of blood pressure, and more particularly to a method and apparatus for removing artifact while taking blood pressure measurements.

2. Background of the Invention

Automatic blood pressure monitors are commonly used to periodically measure the blood pressure of a patient. In most automatic blood pressure monitors, a pressure cuff is attached to a patient's arm over the brachial artery. The cuff is first pressurized with an applied pressure that is high enough to substantially occlude the brachial artery. The cuff pressure is then gradually reduced, either continuously or in increments. As the pressure is reduced to systolic pressure, the flow of blood through the brachial artery beneath the cuff increases substantially.

When the blood flows through the brachial artery following each contraction of the heart, it imparts a pulsatile movement to the wall of the artery. This pulsatile movement is coupled to the blood pressure cuff extending over the artery as minute changes in the cuff pressure, which are known oscillometric pulses. Automatic blood pressure monitors measure and record the amplitude of the oscillometric pulses at a number of cuff pressures. After the blood pressure measurement has been completed, a table, referred to as the oscillometric table, is formed containing the peak oscillometric pulse amplitudes recorded at each cuff pressure.

In theory, the systolic, diastolic, and mean arterial blood pressure can then be determined from the values in the table using theoretical and/or empirical definitions of these parameters as a function of the amplitudes of these oscillometric pulses. However, blood pressure measurements are often adversely affected by artifact, produced by patient movement, shiver, or arrhythmias. Motion-induced artifact can substantially alter the measured amplitude of oscillometric pulses, thus introducing inaccuracies in the measurement of the patient's blood pressure.

In some blood pressure measurement systems where the applied pressure is bled down in steps, at each step the peak amplitude of the oscillations is detected. By measuring the time elapsing between successive peaks, the heart rate can be calculated.

Oscillometric values generally increase from low values at applied pressures above the systolic to a maximum value at applied pressures between systolic and diastolic. Similarly, the values generally increase from low values at applied pressures less than diastolic to the maximum value. Current methods generally choose the largest entry in the oscillometric table as this maximum value. However, artifact will result in spurious high or low values in the table and may be mistaken for the true maximum value in the table, causing erroneous determinations of systolic and diastolic blood pressures. It is desirable therefore to detect and eliminate these spurious high and low values in the table.

As mentioned above, artifact induced noise often obscures the maximum oscillometric peak by either making the maximum oscillometric pulse appear to be smaller or by making other oscillometric pulses appear to be larger, creating a number of local maxima, i.e., values adjacent to lesser values. It is often not possible to determine which of these maxima is the true "maximum" oscillometric peak by direct measurement. Since the systolic, diastolic, and mean pressures are a function of the maximum oscillometric pulse, this can result in inaccurate readings.

SUMMARY OF THE INVENTION

The primary object of the invention is to provide a method and apparatus for allowing an automatic pressure monitor to accurately determine the true maximum of the oscillometric table in the presence of artifact.

It is another object of the invention to provide a method and apparatus for allowing an automatic blood pressure monitor to accurately determine the true maximum of the oscillometric table using the same data that is already collected in conventional automatic blood pressure monitors.

These and other objects of the invention are provided by a system for determining the blood pressure of a patient using data collected by an automatic blood pressure monitor. This system includes such conventional components such as a blood pressure cuff, an air pump, a valve and a pressure transducer in fluid communication with the blood pressure cuff. The pressure transducer generates a signal indicative of the steady state fluid pressure in the blood pressure cuff and the amplitude of oscillometric pulses detected in the cuff. A processor energizes the air pump to inflate the blood pressure cuff, periodically energizes the valve to incrementally reduce the stead state fluid pressure in the blood pressure cuff and records each pressure of the blood pressure cuff at which a measurement was taken as well as the peak amplitude of the oscillometric pulses at that cuff pressure. At the end of the blood pressure measurement, the processor has recorded a table of cuff pressures and corresponding peak oscillometric pulse amplitudes.

After the table has been completed, the processor then examines the table as a whole by determining all local maxima of the peak amplitudes of the oscillometric pulses in the table, the processor also determines the longest sequence of the peak amplitudes of the oscillometric pulses adjacent to each of the local maxima. The sequences examined are sequences of decreasing amplitudes on each side of the local maxima. Once the longest sequences are determined, the processor adds the number of peak amplitudes in the longest sequence of decreasing amplitudes on the right side with the number of peak amplitudes in the longest sequence of decreasing amplitudes on the left side to obtain a total number of peak amplitudes for each of the local maxima. The processor then chooses a true maximum value from one of the local maxima in the table by comparing the total number of peak amplitudes for each local maxima and selecting the local maxima having the largest total number of amplitudes. The processor then calculates the diastolic blood pressure, systolic blood pressure, mean blood pressure and the heart rate, after it has discarded from the table all entries that are not part of the sequences adjacent to the true maximum value.

DETAILED DESCRIPTION OF THE INVENTION

Figure 1:
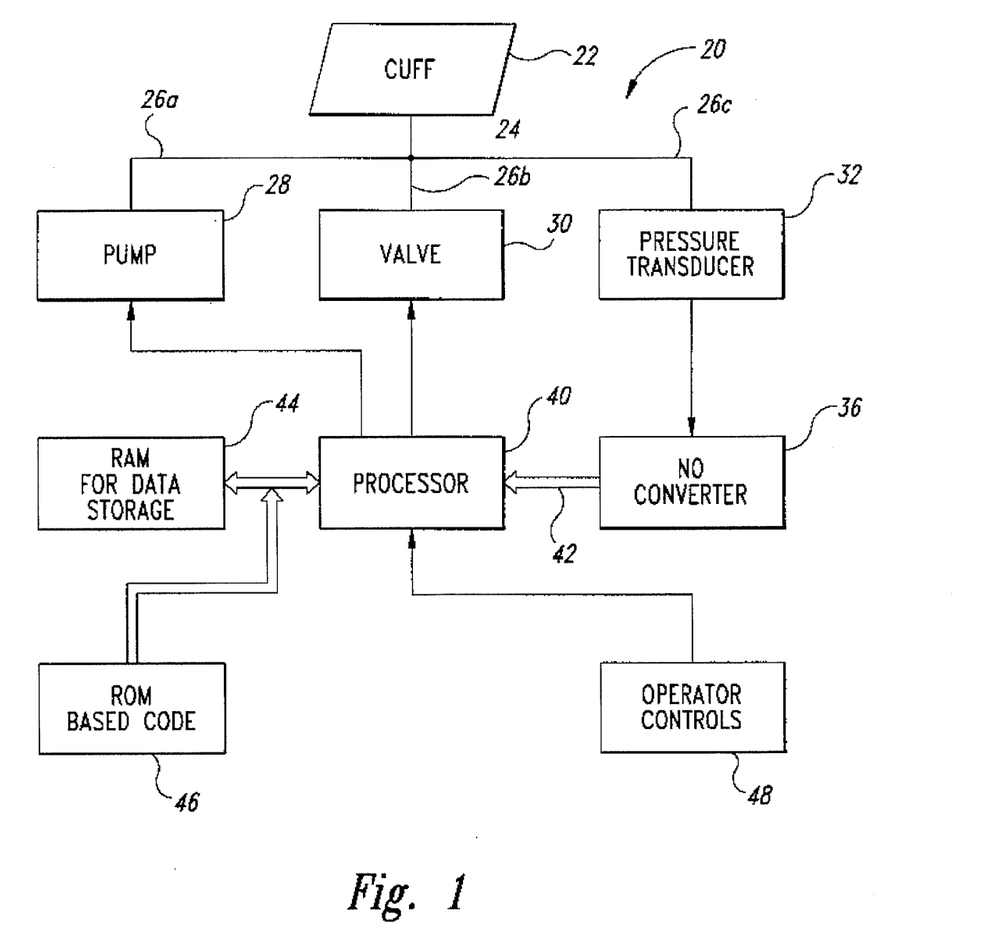
FIG. 1 is a block diagram of one embodiment of the inventive system for automatically making oscillometric blood pressure measurements.

One embodiment of an automatic blood pressure monitor 20 using the inventive artifact rejection method and apparatus is illustrated in FIG. 1. The monitor 20 is composed of a number of hardware components, all of which are conventional. The monitor includes a conventional blood pressure cuff 22 in fluid communication through tubes 24 and 26 with a conventional pump 28, a conventional solenoid valve 30, and a conventional pressure transducer 32. The pump 28 and solenoid valve 30 are electrically connected to respective output ports of a conventional microprocessor 40, which controls the operation of the pump 28 and solenoid valve 30 in a conventional manner.

During the operation of the automatic blood pressure measuring system, the pump 28 inflates the blood pressure cuff 22 to a pressure that is greater than the expected systolic pressure, as indicated by the pressure transducer 32. The solenoid valve 30 is then opened, usually for a predetermined period, although it may be continuously open to allow a slight leakage of air from the blood pressure cuff 22. However, the valve 30 normally allows air to escape from the cuff 22 fairly rapidly in relatively small increments. As the pressure in the cuff 22 is reduced, either gradually or incrementally, the pressure in the cuff 22 is measured by the pressure transducer 32.

The pressure in the blood pressure cuff 22 consists of two components, namely, a relatively constant, or "DC", component and a relatively variable, or "AC", component. The relatively constant component defines the occlusive force of the blood pressure cuff 22. The relatively variable component is produced by pressure pulses in the brachial artery beneath the cuff 22 which impart minute changes in the pressure of the cuff 22 following each contraction of the heart. Thus, the relatively constant DC component of the pressure in the cuff can be used as an indication of cuff pressure, while the relatively variable AC component of the pressure in the cuff 22 can be used to determine the amplitude of an oscillometric pulse.

A signal obtained from the pressure transducer 32 is supplied to a conventional analog-to-digital (A/D) converter 36, where it is digitized and sent through a bus 42 for use by the microprocessor 40. In many modern blood pressure devices, the A/D converter 36 is actually contained on the microprocessor chip. Whether the A/D converter 36 is on the microprocessor chip or whether it is located on a separate chip, the microprocessor 40 has access to a digitized signal indicative of the output from the pressure transducer 32.

The microprocessor 40 extracts the two components of the pressure in the blood pressure cuff 22, namely, (a) the pressure within the cuff, and (b) the minute change in the pressure of the cuff 22 following each contraction of the heart. Alternatively, the separation of the cuff pressure into these two components can be accomplished by external hardware filters, as is quite common in older automatic blood pressure monitors. Whether the separation is accomplished by external hardware filters or by an algorithm internal to the microprocessor 40 is not important for the current invention.

As mentioned above, the microprocessor 40 is of conventional variety and, as is typical with such devices, is connected to a random access memory 44, used for the storage of data, and to either random access memory or read-only memory 46 that contains the software for operating the microprocessor 40. Operator controls 48, such as a keyboard or buttons, are also connected to the microprocessor 40.

Figure 2:
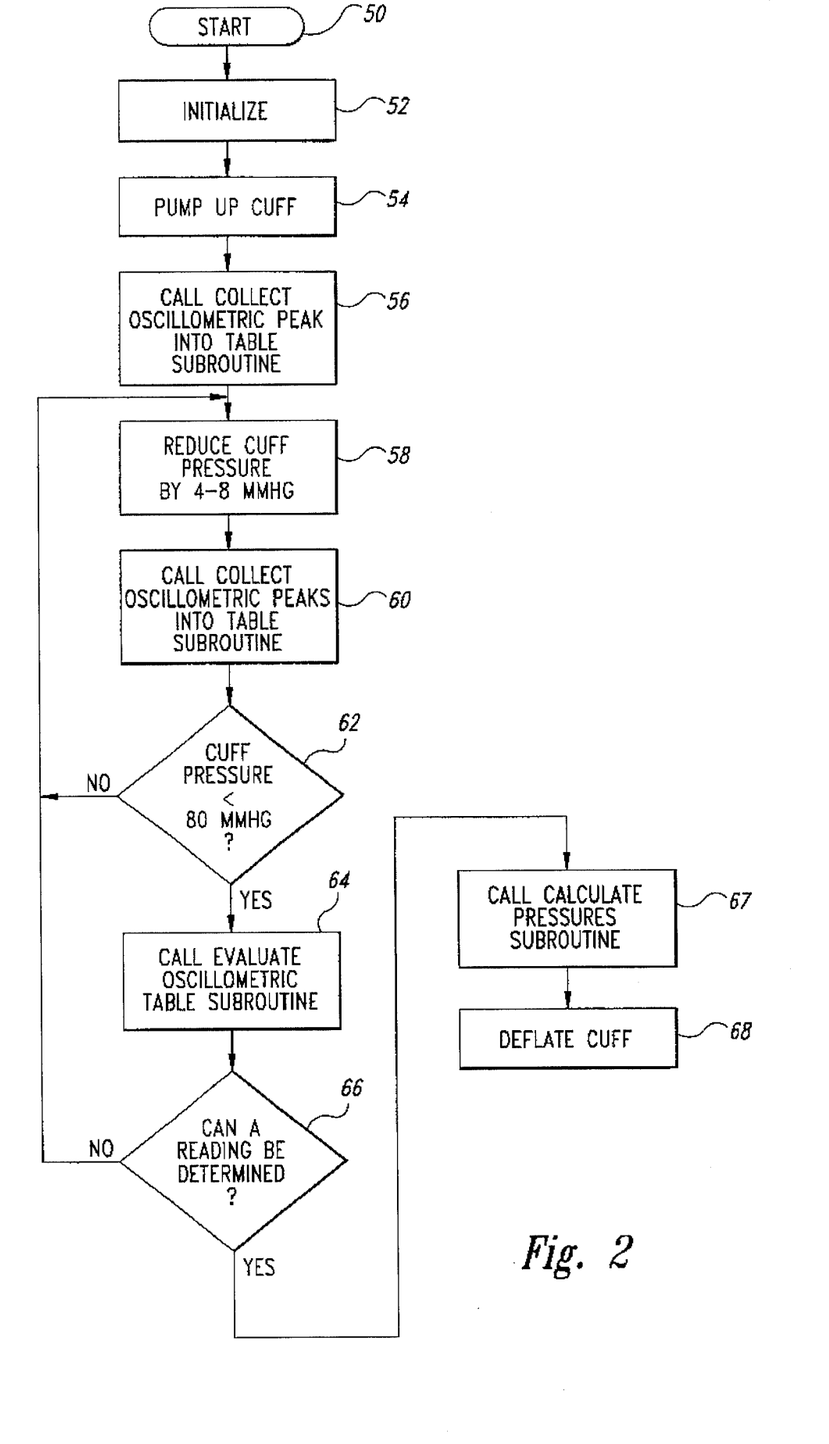
FIG. 2 is a flow chart of software used to program a microprocessor used in the system of FIG. 1.

As explained above, the microprocessor 40 is controlled by software that is stored in a series of program instructions in the memory 46. Flow charts from which object code can be easily and quickly written by one skilled in the art are illustrated in FIGS. 2, 3, 5, and 7. With reference to FIG. 2, the main program starts at 50, either through an operator command, automatically at power-up, or when called by another program stored in the memory 46. As is conventional with microprocessor-based systems, the microprocessor 40 (FIG. 1) is initialized at step 52 to set up the software for subsequent processing, such as, for example, by establishing tables that will subsequently contain data, by setting flags and by setting variables to known values. The microprocessor 40 applies a signal to the air pump 28 in step 54 to inflate the cuff 22. At the same time, the microprocessor 40 periodically samples the output of the A/D converter 36 to monitor the cuff pressure. The step 52 also includes the step of calculating a target for the cuff pressure, such as greater than systolic, or often to a predetermined level, for example, 165 millimeters of mercury. Then microprocessor 40 continues to apply the signal to the air pump 28 until the cuff pressure has reached the target value.

Figure 3:
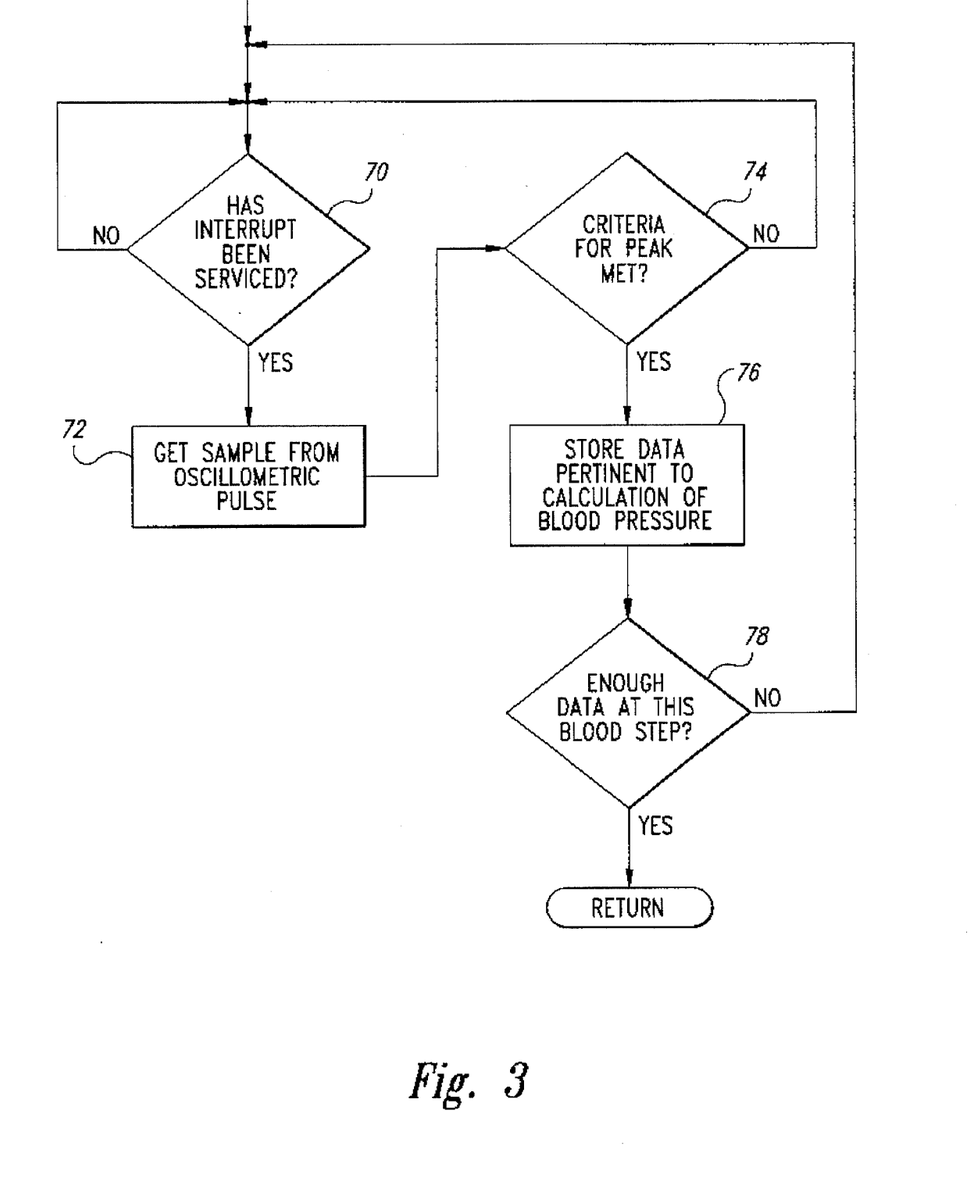
FIG. 3 is a flow chart of software used by the microprocessor of FIG. 1 to determine the peak oscillometric pulse at a given steady state pressure.

Proceeding from these steps, the main program calls a subroutine in step 56 that collects an oscillometric peak and places it into a table. The steps of the subroutine for collecting an oscillometric peak are shown in FIG. 3 and require the microprocessor 40 being interrupt driven in a conventional manner so that it periodically performs a clock driven interrupt service routine. With reference to FIG. 3, the subroutine called at step 56 is entered at step 70 in which it remains in a loop until the interrupt has been serviced. The subroutine then proceeds to step 72 where the digitized signal representing the minute changes in the pressure of the cuff is processed, the proper criteria for a set of samples being considered an oscillometric peak is established, and outputs corresponding to the processed digitized signal and oscillometric peak criteria are generated. The subroutine then checks at step 74 to see if the criteria established at step 72 have been met. The criteria for determining if a set of samples is characteristic of an oscillometric peak are conventional and are thus not explained herein. If the samples are not characteristic of an oscillometric peak, the subroutine returns to step 70 to await another interrupt. If the samples do have the characteristic of an oscillometric peak, the subroutine branches to step 76 to store the amplitude of the oscillometric peak in the table along with the current cuff pressure so that the amplitude of the oscillometric peak is correlated with the cuff pressure at which the oscillometric pulse occurred. The subroutine then checks at step 78 to see if enough data has been collected at the current cuff pressure, i.e., does the oscillometric peak meet the amplitude or timing constraints of the algorithm? If enough data have not been collected, the subroutine returns to step 70 to await another interrupt, and then collects another sample at step 72 as explained above before, once again checking for sufficient data at step 78. If the subroutine determines at step 78 that all the pertinent data for each oscillometric peak have been collected, the subroutine exits and returns to the main program at step 58, as shown in FIG. 2.

Returning to FIG. 2, after the initial oscillometric peak has been recorded, the program in step 58 opens solenoid valve 30 and reduces the cuff pressure by four to eight mm Hg. The program then once again calls the subroutine of FIG. 3 in step 60 to collect into the table a new value for an oscillometric peak. After returning to the main program, the program proceeds to step 62 where it tests to determine if the cuff pressure is less than 80 mm Hg. The program will continue to loop through steps 58–62 until the cuff pressure has dropped below 80 mm Hg. Once the main program determines at step 62 that the cuff pressure has reached the pressure level of 80 mm Hg, the program proceeds to step 64 where it calls a subroutine that evaluates the oscillometric table.

The data stored in the table after sufficient data have been obtained may appear for example as:

| CUFF PRESSURE | PULSE AMPLITUDE |
|---|---|
| 150 | 0 |
| 140 | 5 |
| 130 | 9.2 |
| 120 | 10 |
| 110 | 9.7 |
| 100 | 7.5 |
| 90 | 5 |
| 80 | 2.5 |
| 70 | 0 |

The interval between oscillometric pulses are also stored and these data are used to calculate the heart rate.

Figure 4:
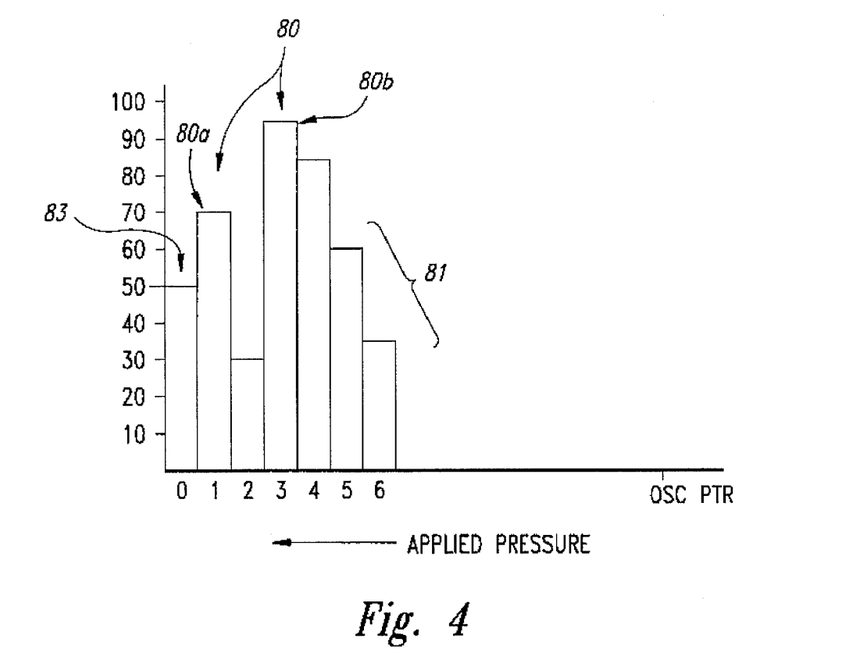
FIG. 4 is a graphic representation of a table formed during the operation of the system of FIG. 1 using the program of FIG. 2.

FIG. 4 is a graphical representation of the contents of a table, similar to the one above, showing the oscillometric peak at each applied pressure. In the Figure there are two local maxima 80, i.e., an entry that is larger than the point to the left and to the right of it. The following subroutine acts on the assumption that true oscillometric peaks should form a series of increasing values from above systolic pressure to the mean pressure, and a series of decreasing values from the mean pressure to below diastolic pressure. On the basis of this assumption, the inventive method and apparatus is able to determine accurate approximations of the true oscillometric peaks from artifact affected data of the type shown in FIG. 4.

Figure 5:
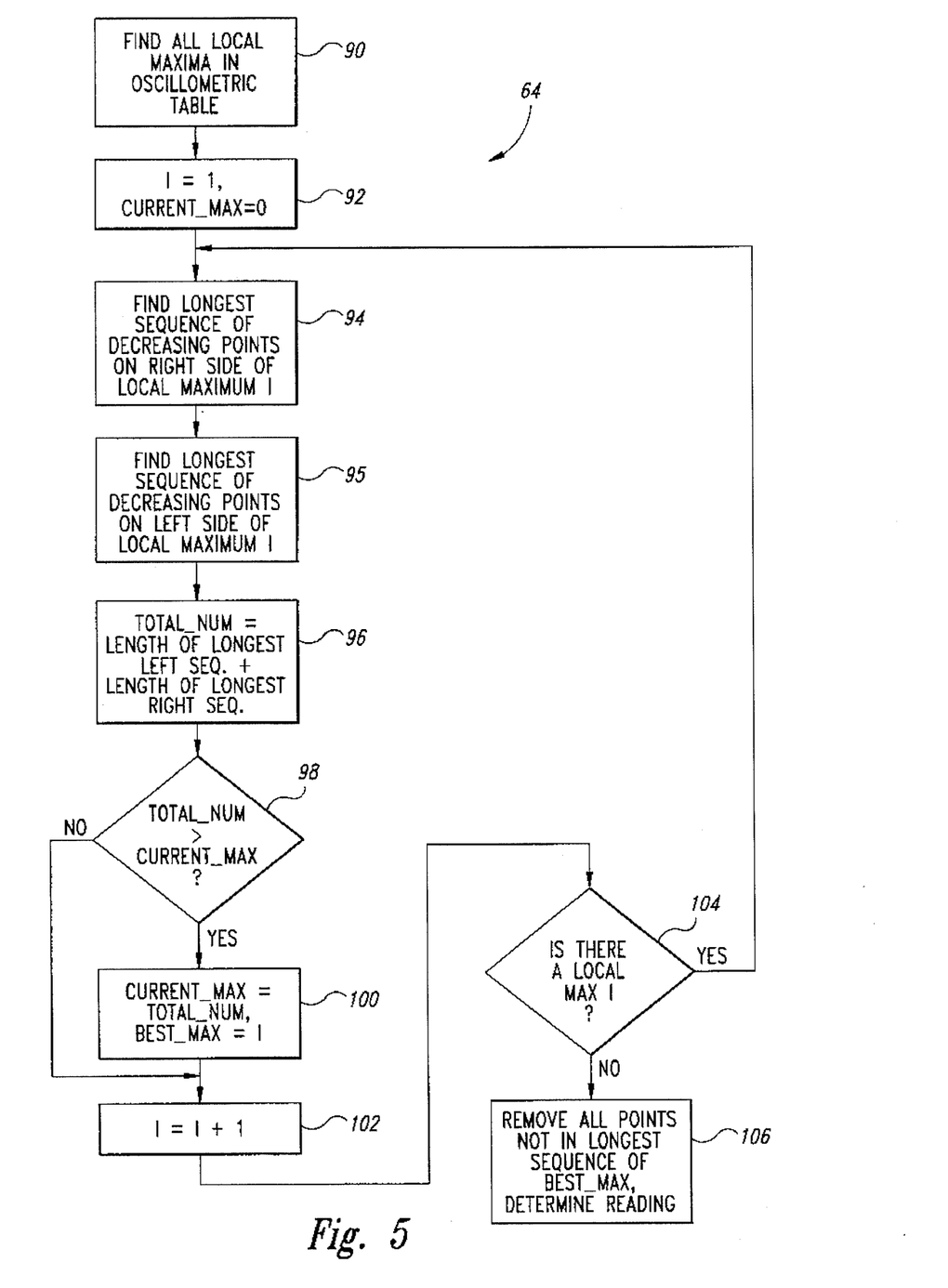
FIG. 5 is a flow chart of a subroutine called by the program of FIG. 2 to evaluate an oscillometric table of the type shown in FIG. 4.

FIG. 5 is a flow chart of the subroutine called by the main program at step 64 (FIG. 2) for evaluating the oscillometric table. With reference to FIG. 5, the subroutine is entered at step 90 where it identifies all of the local maxima 80 in the oscillometric table. In this step, each one of the local maxima 80 is assigned an index number 1 through n, for example, the maxima 80a (shown in FIG. 4) would be assigned I=1, and 80b assigned I=2. Next, at step 92, the value I is set equal to 1, and the value current max, discussed below, is set to zero. The program then proceeds to step 94 where, for each local maxima 80 in the oscillometric table, the program finds the number of oscillometric peaks in the longest sequence of decreasing amplitudes from the right side of the designated maxima 80. The number of peaks in this sequence is assigned to a variable RIGHT NUM. Then in step 95, the number of peaks in the longest decreasing sequence of amplitudes from the left side of the designated maxima 80 are determined and assigned to a variable LEFT NUM. The value of RIGHT NUM and LEFT NUM for the designated maxima 80 are then added in step 96 to obtain a value of TOTAL NUM. In step 98, the value of TOTAL NUM is compared against the value of CURRENT MAX, which was initially set to zero in step 92. If the value of TOTAL NUM exceeds CURRENT MAX, then the value of CURRENT MAX is updated in step 100 to become the current value of TOTAL NUM. Further, in the step of 100, a variable BEST MAX is set equal to the value I of the maxima 80 that was found in step 98 to have a TOTAL NUM which exceeded the CURRENT MAX. The value I is then incremented by one in step 102. However, if the subroutine determines at step 98 that the value of TOTAL NUM for the current maxima 80 does not exceed the value of CURRENT MAX, then step 100 is bypassed and I is immediately incremented by one in step 102. In step 104, the program checks to see if there is another maxima 80 corresponding to the newly incremented value of I. For example, if I were equal to 1 prior to step 102 and then incremented to a value of 2 in step 102, step 104 would look to see if there is a maxima corresponding to the value of I=2, which in this case as shown in FIG. 4 would correspond to the value 80b. The program will continue to loop through steps 94–104 until the TOTAL NUM for each local maxima 80 has been compared with each other maxima 80 in the table.

The subroutine of FIG. 5 would process a table corresponding to the example shown in FIG. 4 in the following manner. First, the index number I is incremented to 1 in step 92 and the corresponding maxima 80a is examined in steps 94 and 95. These steps determine that there are only two peaks 81 in the longest decreasing sequence of amplitudes from the right of maxima 80a, so RIGHT NUM=2, and there is only one peak 83 in the longest decreasing sequence of amplitudes from the left of 80a, so LEFT NUM=1. Accordingly, the TOTAL NUM of maxima 80a would equal 3 and would replace the initial zero value of CURRENT MAX in step 100. In step 102 the value I is incremented to 2. Then in the second loop of steps 94–104, the variable RIGHT NUM for maxima 80b would equal 3, while the variable LEFT NUM for maxima 80b would equal 2, yielding a value for TOTAL NUM of 5, which is greater than the value of TOTAL NUM for maxima 80a. Thus, in step 100 the variable CURRENT MAX would be set to 5 and the variable BEST MAX would be reset to 2. The subroutine will then proceed to step 102 and increment I to 3. After the incremental step of 102, the step of 104 will test to determine if there is a maxima corresponding to the value 3 and in the present example no such value exists. Once the subroutine determines at step 104 that there are no more local maxima to evaluate, the subroutine proceeds to step 106.

Figure 6:
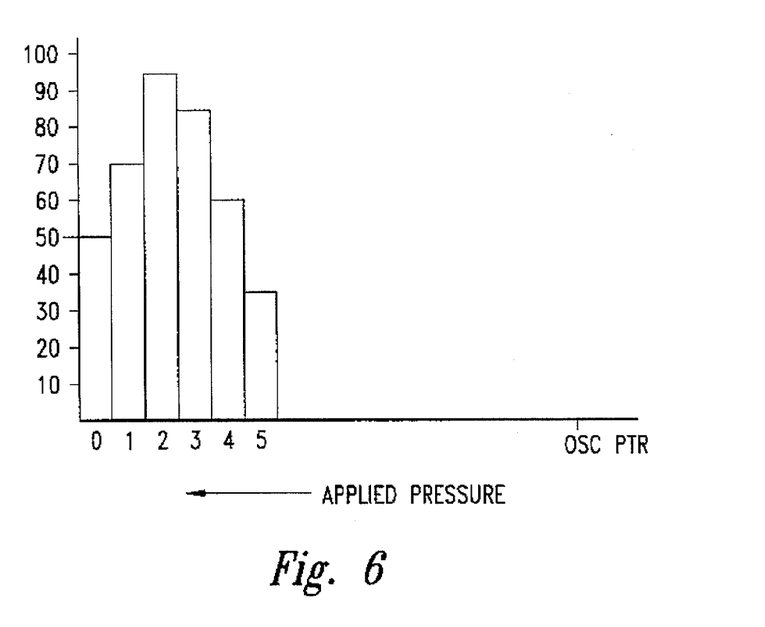
FIG. 6 is a graphic representation of the remaining table of values which are used to determine the systolic, diastolic, mean and heart rate.

In step 106, the subroutine removes all entries from the table that are not the true maximum or part of the longest sequences corresponding to the chosen true maximum. This leaves a raw table with decreasing entries from the true maximum to the ends, as shown in FIG. 6. The subroutine then exits and returns to step 66 of the main program shown in FIG. 2. In this step 66, the program tests to see if a reading can be determined. If a reading cannot be determined, the program returns to step 58, and new oscillometric peaks are collected into the table in steps 58–64, as explained above.

Figure 7:
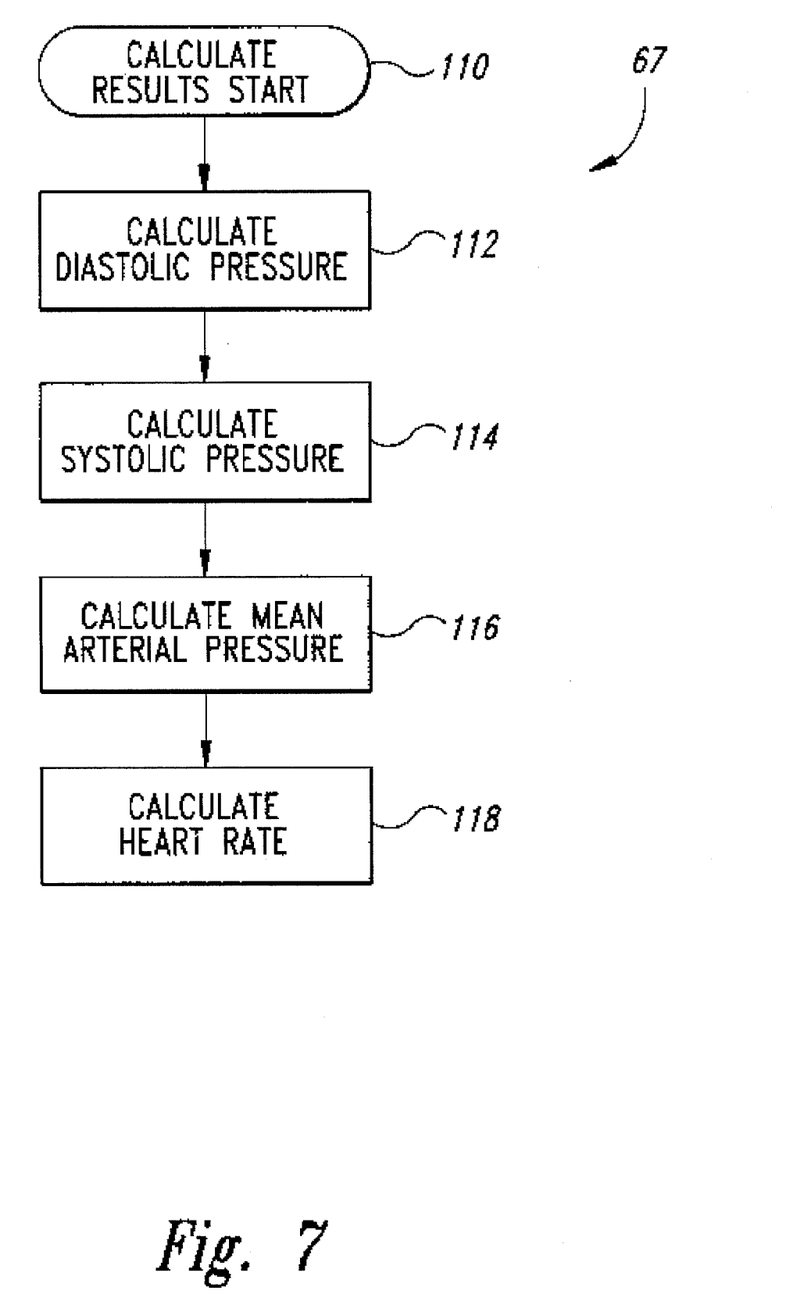
FIG. 7 is a flow chart of software used by the microprocessor of FIG. 1 to determine the diastolic, systolic and mean blood pressure as well as the heart rate of a patient.

However, if a reading can be determined, then the program calls at step 67 a subroutine for calculating pressures, which is shown in FIG. 7.

With reference to FIG. 7, the "calculate results" subroutine is entered at step 110, and the diastolic pressure is calculated in a conventional manner from the data in the table after being corrected for artifact in steps 94–106 of FIG. 5 at step 112. The "calculate results" subroutine then progresses to step 114 to calculate the systolic pressure in a conventional manner from the corrected data. The program then proceeds to step 116 where it calculates the mean arterial pressure in a conventional manner from the data in the table that has been corrected for artifact, as described above. The heart rate is calculated in step 118 by a conventional process, and the subroutine then returns to the main program (FIG. 2) at step 68. Finally, as shown in FIG. 2, the cuff is deflated in step 68 and the process of measuring the blood pressure and heart rate is terminated.

It is thus seen that the inventive method and apparatus for determining the arterial blood pressure of a patient utilizes hardware found in conventional automatic blood pressure monitors and it calculates the arterial pressure using the same method that conventional blood pressure monitors already use to obtain and to calculate the diastolic and systolic blood pressures. Furthermore, the system is able to accurately determine the mean arterial pressure, and the systolic and diastolic pressures, despite the presence of artifact in the monitoring process by examining an entire oscillometric table, determining a true maximum oscillometric peak and discarding erroneous values.

While the foregoing has been a discussion of a specific embodiment of the present invention, those skilled in the art will appreciate that numerous modifications to the disclosed embodiment may be made without departing from the spirit and scope of the invention. Accordingly, the invention is limited only to the following claims.

I claim:

1. A blood pressure monitor, comprising:

a blood pressure cuff;

an air pump in fluid communication with said blood pressure cuff to direct pressurized air into said cuff;

a valve in fluid communication with said blood pressure cuff to selectively vent said cuff to atmosphere;

a pressure transducer in fluid communication with said blood pressure cuff, said pressure transducer generating a signal indicative of a steady state fluid pressure in said blood pressure cuff corresponding to an occlusive pressure exerted by said blood pressure cuff on an artery and a transient fluid pressure in said blood pressure cuff indicative of the amplitude of an oscillometric pulse;

an analog-to-digital converter connected to said pressure transducer for sampling the output of said pressure transducer and generating respective digital samples corresponding to the output of said pressure transducer; and a processor electrically connected to said air pump, said valve and said analog-to-digital converter, said processor receiving the respective digital samples corresponding to the signal indicative of the steady state fluid pressure in said blood pressure cuff and the amplitude of the oscillometric pulses, said processing device energizing said air pump to inflate said blood pressure cuff, selectively energizing said valve to reduce the steady state fluid pressure in said blood pressure cuff, recording in a table the steady state fluid pressure and the amplitude of a peak of the oscillometric pulses at such pressure, determining all local maxima of the oscillometric peaks in the table, determining the longest sequences of oscillometric peaks adjacent to each of the local maxima, selecting one of the local maxima as a true maximum value based on a comparison of the longest sequences of oscillometric peaks at cuff pressures adjacent to and above and below the cuff pressure at which each of the local maxima occurred; and computing at least one of the diastolic blood pressure, the systolic blood pressure, and the mean blood pressure based on the true maximum value.

2. The blood pressure monitor of claim 1 wherein the determining of the longest sequences of oscillometric peaks adjacent to each of the local maxima by said processor comprises:

finding the longest sequence of oscillometric peaks having amplitudes that are in sequentially decreasing order taken at cuff pressures that increase from the cuff pressure at which the local maxima was obtained; and finding the longest sequence of oscillometric peaks having amplitudes that are in sequentially decreasing order taken at cuff pressures that decrease from the cuff pressure at which the local maxima was obtained.

3. The blood pressure monitor of claim 2 wherein the selecting of the true maximum value by said processor comprises:

adding the number of the oscillometric peaks in the longest sequence of decreasing amplitudes taken at cuff pressures above the cuff pressure at which the local maxima was obtained with the number of oscillometric peaks in the longest sequence of decreasing amplitudes taken at cuff pressures below the cuff pressure at which the local maxima was obtained to determine a total number of oscillometric peaks for each maxima;

comparing the total number of oscillometric peaks for each maxima; and choosing as the true maximum the maxima having the largest total number.

4. The blood pressure monitor of claim 1 wherein said processor further creates a modified table by discarding from the table of the peak oscillometric pulses all data except the local maxima chosen as the true maximum and the longest oscillometric peak sequences used to choose the local maxima as the true maximum.

5. The blood pressure monitor of claim 4 wherein the processor computes at least one of the diastolic blood pressure, the systolic blood pressure and the mean blood pressure using the modified table.

6. A method for using a blood pressure monitor of the type having a blood pressure cuff, an air pump in fluid communication with the cuff to direct pressurized air into the cuff, a valve in fluid communication with the cuff to selectively vent the cuff to atmosphere, a pressure transducer in fluid communication with said cuff generating an output including a pressure signal indicative of a steady state fluid pressure in the cuff corresponding to an occlusive pressure exerted by said cuff on an artery and a transient fluid pressure in said cuff indicative of an amplitude of an oscillometric pulse, a processor in electrical communication with said air pump and said valve for selectively energizing said air pump or valve to pressurize or depressurize said cuff, respectively, said method comprising:

setting the steady state fluid pressure in said cuff to an initial value;

selectively energizing the air valve to reduce the steady state fluid pressure in the cuff;

sampling the pressure signal output by said pressure transducer resulting from variations in the fluid pressure in the cuff caused by the oscillometric pressure pulses;

recording in a table the steady state fluid pressure at which each sample is taken and the amplitude of the peak oscillometric pressure pulses at such steady state fluid pressure;

determining all local maxima of the oscillometric peaks in the table;

determining the longest sequences of the oscillometric peaks at cuff pressures adjacent to and above and below the cuff pressure at which each of the local maxima occurred;

selecting one of the local maxima as a true maximum value based on a comparison of the longest sequences adjacent to each of the local maxima; and computing at least one of the diastolic blood pressure, the systolic blood pressure, and the mean blood pressure based on the true maximum value.

7. The method of claim 6 wherein said step of determining the longest sequences adjacent to each of the local maxima comprises:

finding the longest sequence of oscillometric peaks having amplitudes that are in sequentially decreasing order taken at cuff pressures that increase from the cuff pressure at which the local maxima was obtained; and finding the longest sequence of oscillometric peaks having amplitudes that are in sequentially decreasing order taken at cuff pressures that decrease from the cuff pressure at which the local maxima was obtained.

8. The method of claim 7 wherein said step of selecting the true maximum comprises:

adding the number of the oscillometric peaks in the longest sequence of decreasing amplitudes taken at cuff pressures above the cuff pressure at which the local maxima was obtained with the number of oscillometric peaks in the longest sequence of decreasing amplitudes taken at cuff pressures below the cuff pressure at which the local maxima was obtained to determine a total number of oscillometric peaks for each maxima;

comparing the total number of oscillometric peaks for each maxima; and choosing as the true maximum the maxima having the largest total number.

9. The method of claim 6 wherein said method further comprises the step of:

creating a modified table by discarding from the table formed during said recording step all data except the local maxima chosen as the true maximum and the longest oscillometric peak sequences used to choose the local maxima as the true maximum.

10. The method of claim 9 wherein said computing step is performed using the modified table.

11. A blood pressure monitor, comprising:

a blood pressure cuff;

an air pump in fluid communication with said blood pressure cuff to direct pressurized air into said cuff;

a valve in fluid communication with said blood pressure cuff to selectively vent said cuff to atmosphere;

a pressure transducer in fluid communication with said blood pressure cuff, said pressure transducer generating a signal indicative of a steady state fluid pressure in said blood pressure cuff corresponding to an occlusive pressure exerted by said blood pressure cuff on an artery and a transient fluid pressure in said blood pressure cuff indicative of the amplitude of an oscillometric pulse;

a processor electrically connected to said air pump and said valve, said processor receiving the signal indicative of the steady state fluid pressure in said blood pressure cuff and the amplitude of the oscillometric pulses, said processor energizing said air pump to inflate said blood pressure cuff to an initial value, selectively energizing said valve to reduce the steady state fluid pressure in said blood pressure cuff to a plurality of pressures recording in a table the steady state fluid pressure and the amplitude of a peak of the oscillometric pulses at each pressure, determining all local maxima of the oscillometric peaks in the table, counting each of the oscillometric peaks in the longest sequence of decreasing amplitudes at cuff pressures above and below the cuff pressure at which the local maxima was obtained, adding each of the oscillometric peaks counted for the local maxima to determine a total number of peaks for each maxima, comparing the total number of peaks for each maxima, selecting one of the local maxima as a true maximum value by choosing the maxima having the largest total number of peaks, modifying the table by retaining from the table only the oscillometric peaks of the true maximum value and the peaks in the longest sequence of decreasing amplitudes at cuff pressures above and below the cuff pressure at which the local maxima was obtained, and computing at least one of the diastolic blood pressure, the systolic blood pressure and the mean blood pressure using the modified table.

* * * * *